United States Patent [19]

Harandi et al.

[11] Patent Number: 5,106,389
[45] Date of Patent: Apr. 21, 1992

[54] PROCESS FOR CONVERSION OF LIGHT PARAFFINS TO ALKYLATE IN THE PRODUCTION OF TERTIARY ALKYL ETHER RICH GASOLINE

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 599,199

[22] Filed: Oct. 17, 1990

[51] Int. Cl.$^5$ .............................. C10L 1/18
[52] U.S. Cl. ...................... 44/449; 568/697
[58] Field of Search ......................... 44/449

[56] References Cited

U.S. PATENT DOCUMENTS

| 4,016,218 | 4/1977 | Haag et al. | 585/467 |
| 4,544,777 | 10/1985 | Hutson, Jr. et al. | 44/449 |
| 4,684,757 | 8/1987 | Avidan et al. | 585/331 |
| 4,754,100 | 6/1988 | Sorensen et al. | 585/708 |
| 4,788,365 | 11/1988 | Harandi et al. | 585/312 |
| 4,826,507 | 5/1989 | Harandi et al. | 44/449 |
| 4,827,046 | 5/1989 | Harandi et al. | 585/310 |
| 4,854,939 | 8/1989 | Harandi et al. | 44/449 |
| 4,899,008 | 2/1990 | LaPierre et al. | 585/467 |
| 5,001,292 | 3/1991 | Harandi et al. | 44/449 |
| 5,024,679 | 6/1991 | Harandi et al. | 44/449 |

Primary Examiner—Prince Willis, Jr.
Assistant Examiner—Ellen McAvoy
Attorney, Agent, or Firm—Alexander J. McKillop; Charles J. Speciale; L. G. Wise

[57] ABSTRACT

A process is disclosed for the production of high octane alkyl tertiary alkyl ether rich gasoline and gasoline rich in alkylated aromatics. It is disclosed that unreacted $C_3-C_4$ hydrocarbon fraction of etherification feedstock plus unreacted alkanol can be separated and employed as alkylating agents in combination with a feedstream containing light aromatics when the alkylation reaction is carried out under conditions of high severity in contact with a high activity shape selective metallosilicate catalyst such as ZSM-5. Under high severity conditions olefin-assisted paraffin conversion also occurs as well as cracking, redistribution and alkylation. Aromatic rich gasoline is a suitable feedstream to the high severity conversion zone to produce a gasoline rich in alkylated aromatics.

18 Claims, 3 Drawing Sheets

PROCESS FOR CONVERSION OF LIGHT PARAFFINS TO ALKYLATE IN THE PRODUCTION OF TERTIARY ALKYL ETHER RICH GASOLINE

This invention relates to an integrated process for the production of gasoline boiling range hydrocarbons containing alkyl tertiary alkyl ethers and alkylated aromatics. The invention particularly relates to a process integration for converting light paraffins in an iso-olefin rich feedstock to alkyl aromatics and higher hydrocarbon gasoline components while producing high octane gasoline rich in tertiary alkyl ether. More particularly, the invention relates to the conversion of $C_{3}+$ feedstock to $C_{5}+$ gasoline containing methyl tertiary butyl ether (MTBE) and tertiary amyl methyl ether (TAME) and an alkylated aromatic rich gasoline.

BACKGROUND OF THE INVENTION

It is known that isobutylene and other isoalkenes, or iso-olefins, produced by hydrocarbon cracking may be reacted with methanol and other C1-C4 lower aliphatic alcohols, or alkanol, over an acidic catalyst to provide methyl tertiary butyl ether (MTBE) or the like. Generally, it is known that asymmetrical ethers having the formula $(CH_3)_3C-O-R$, where R is a C1-C4 alkyl radical, are particularly useful as octane improvers for liquid fuels, especially gasoline.

MTBE, ethyl t-butyl ether (ETBE), tert-amyl methyl ether (TAME) and isopropyl t-butyl ether (IPTBE) are known to be high octane ethers. The article by J. D. Chase, et al., *Oil and Gas Journal*, Apr. 9, 1979, discusses the advantages one can achieve by using such materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

In recent years, a major development within the petroleum industry has been the discovery of the special catalytic capabilities of a family of zeolite catalyst based upon medium pore size shape selective metallosilicates. Discoveries have been made leading to a series of analogous processes drawn from the catalytic capability of zeolites. Depending upon various conditions of space velocity, temperature and pressure lower oxygenates, such as methanol can be converted in the presence of zeolite type catalyst to olefins which can oligomerize to provide gasoline or distillate or can be converted further to produce aromatics. Recognizing the commonality of the feedstock and product between etherification reactions to produce high octane gasoline and zeolite catalyzed conversion reactions, interest has focused on the applicability of combined processes as an approach to advance the art in the production of high octane gasoline.

It has been discovered that under certain conditions substantial improvements in the art of alkyl tert-alkyl ether production can be realized in a combination or integration of etherification and hydrocarbon conversion processes based upon zeolite type catalysis. In U.S. Pat. Nos. 4,788,365, 4,826,507 and 4,854,939 to M. N. Harandi and H. Owen novel processes are described for carrying out the production of MTBE and TAME wherein unreacted alcohol and light olefin components from the etherification reaction are converted to higher hydrocarbons in contact with zeolite catalyst. These patents are incorporated herein by reference. In these processes the etherification reaction is carried out using $C_{4}+$ hydrocarbon feedstream rich in iso-olefins with the subsequent oligomerization of unreacted light olefins. Feedstreams comprising $C_3$ hydrocarbons are not employed and conversion of light paraffins to higher hydrocarbons is not experienced.

In U.S. Pat. No. 4,754,100 by C. M. Sorensen et al., incorporated herein by reference, an improved process is described for converting propane to higher hydrocarbons such as butanes and $C_5$ aliphatics over zeolite catalyst by adding a monoolefin to the propane feed. In U.S. Pat. application Ser. No. 210,177, filed Jun. 20, 1988 by C. Sorensen et al., incorporated herein by reference, the conversion of normal butane to propane and gasoline over zeolite catalyst is described. Both of these processes for converting light paraffins employing zeolite catalysis are carried out under conditions of high severity at high pressure.

In U.S. patent application Ser. No. 559,739, filed Jul. 30, 1990, by M. N. Harandi et al., incorporated herein by reference, an invention is disclosed comprising a process integration for converting propane and butane in an isoolefin rich feedstock to higher hydrocarbons and high octane gasoline rich in tertiary alkyl ether. The light paraffins conversion is carried out in contact with ZSM-5 zeolite catalyst under high severity conversion conditions. It is also known, as disclosed in U.S. Pat. No. 4,899,008 to R. La Pierre and R. Morrison and incorporated herein by reference, that under the high severity conversion conditions representative of those employed in light paraffins conversion, alkylation of aromatics can be carried out using $C_2$-$C_4$ paraffins as alkylating agents.

It is an object of the present invention to provide an integrated process for the conversion of light paraffins and olefins to tertiary alkyl ethers, higher hydrocarbons, and alkylated aromatics.

Another object of the present invention is to provide a process for the utilization of $C_{3}+$ hydrocarbon feedstreams for the production of tertiary alkyl ether rich gasoline and the conversion of $C_3$ paraffins and olefins to higher hydrocarbons and alkylated aromatics rich gasoline.

Another object of the invention is to reduce benzene in the gasoline pool by alkylating a benzene-rich stream with at least a fraction of the unconverted $C_4$'s from an MTBE unit.

Yet a further object of the present invention is to provide a process for converting $C_{3}+$ feedstock to MTBE rich $C_{5}+$ gasoline while converting light paraffins to alkylated aromatics rich gasoline.

SUMMARY OF THE INVENTION

An integrated continuous process has been discovered for the production of high octane alkyl tertiary alkyl ether rich gasoline and gasoline rich in alkylated aromatics. Through the integrated process of the present invention the feedstock used to produce high octane ethers from iso-olefins and alkanol, typically comprising $C_{4}+$ hydrocarbons, can be expanded to include $C_{3}+$ paraffinic hydrocarbons. It has been discovered that the $C_3$-$C_4$ hydrocarbon fraction of the feedstock which does not react in the etherification step, plus unreacted alkanol, can be separated and usefully employed as alkylating agents in combination with a feedstream containing alkylatable aromatics. This is achieved when the alkylation reaction is carried out under conditions of high severity in contact with a high activity shape selective metallosilicate catalyst such as, preferably, ZSM-5. Alternatively, a small pore size zeolite is used, including ZSM-22, ZSm-23, or ZSM-35, to minimize production of $C_{11}+$ aromatics. Under the selected conditions of high severity olefin-assisted paraffin conversion also occurs as well as cracking, redistribution and alkylation. An aromatic rich gasoline is a suitable feedstream to the high severity conversion zone to produce a gasoline rich is alkylated aromatics.

It has also been discovered that the unreacted $C_3$-$C_4$ paraffinic hydrocarbon and alkanol stream from etherification can first be converted under low severity conditions with zeolite catalyst to oligomerize olefins contained in the unreacted $C_3$-$C_4$ hydrocarbon stream and convert unreacted alkanol to olefins. The paraffinic and olefinic product from the low severity step is then utilized, in whole or in part, in the high severity alkylation step described above.

More particularly, a continuous integrated process has been discovered for producing hydrocarbon streams comprising $C_5+$ gasoline rich in alkyl tertiary alkyl ether and $C_5+$ alkylated aromatic rich gasoline. The process comprises:

(a) contacting alkanol and $C_3+$ aliphatic hydrocarbon stream containing alkanes and alkenes rich in iso-olefins with acid etherification catalyst under iso-olefin etherification conditions in an etherification reaction zone;

(b) separating etherification effluent from step (a) to recover an overhead stream comprising unreacted alkanol plus $C_4-$ aliphatic hydrocarbons and a liquid product stream comprising $C_5+$ gasoline containing alkyl tertiary-alkyl ether;

(c) contacting the overhead stream and a feedstream containing alkylatable aromatic hydrocarbons in an alkylation reactor containing acidic, medium pore metallosilicate catalyst under alkylation conditions and conversion conditions sufficient to convert alkanol, alkane and alkene to higher hydrocarbons. The conditions comprise a temperature of about 200° C. to 400° C. and a pressure above about 3400 kPa; and (d) separating step (c) reaction products and recovering said $C_5+$ alkylated aromatic rich gasoline and a stream comprising $C_4-$ hydrocarbons.

The process of the instant invention is carried out in a novel reactor system comprising an etherification reactor means for etherifying the alkanol and a hydrocarbon feedstream containing iso-olefins. A first fractionation means is receivably connected to the etherification reactor for separating effluent therefrom. A low pressure conversion reactor means is operatively connected to the first fractionation means, for converting an overhead stream containing unreacted alkanol and alkene to higher hydrocarbon. A second fractionation means is receivably connected to the low pressure reactor for separating the effluent therefrom. A high pressure alkylation reactor means is operatively connected to the second fractionation means and also contains means for receiving an alkylatable aromatic feedstream whereby the second fractionator overhead stream and an unalkylated aromatics feedstream is converted to alkylated aromatics gasoline. A third fractionator means is receivably connected to the alkylation reactor and contains means for receiving an unalkylated aromatic rich gasoline feedstream whereby the alkylation reactor effluent and the unalkylated aromatic rich gasoline are fractionated. A conduit means is provided operatively connected to a mid-portion of the third fractionator and to the alkylation reactor means for receiving an alkylatable aromatic feedstream comprising light aromatics, preferably benzene, whereby alkylatable aromatics are passed to the alkylation reactor. Light aromatics in the present invention include $C_7-$ aromatics, particularly benzene.

DETAILED DESCRIPTION OF THE INVENTION

Figure 1:
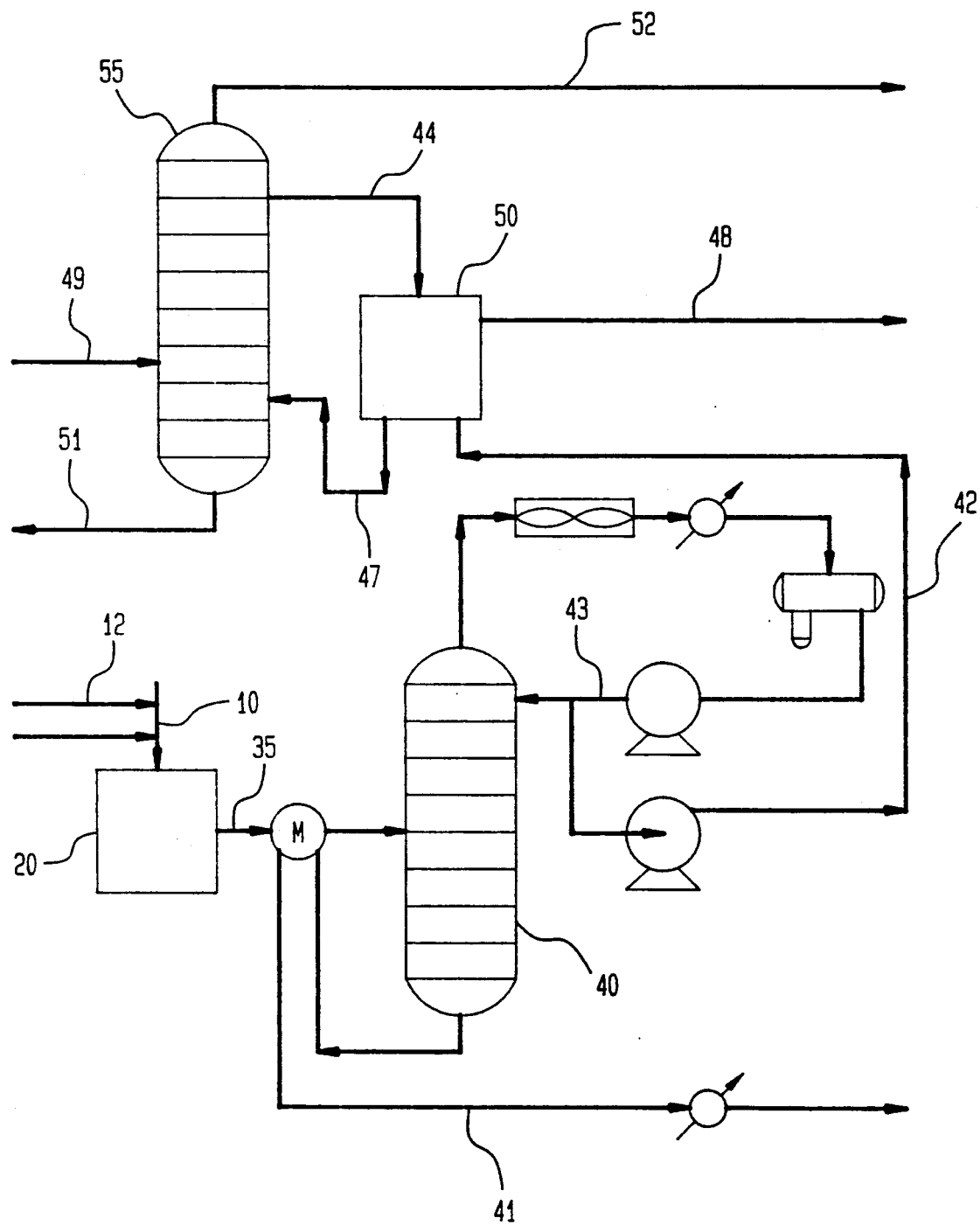
FIG. 1 is a schematic diagram of the invention integrating etherification and high pressure conversion of alkanol and hydrocarbons to alkylated aromatics.

The feedstock to the etherification step of the present invention includes lower alkanol and $C_3+$ hydrocarbons rich in iso-olefins. Typical hydrocarbon feedstock materials for etherification reactions according to the present invention include olefinic streams, such as FCC light cracked gas containing butene isomers and propene in mixture with substantial amounts of paraffins including propane, n-butane and isobutane. The $C_4$ components usually contain a major amount of unsaturated compounds, such as 10-35% isobutylene, 20-55% linear butenes, and small amounts of butadiene. Also, $C_4+$ heavier olefinic hydrocarbon streams may be used, particularly mixtures of isobutylene and isoamylene. Feedstock includes light alkane and alkene hydrocarbons including $C_3+$ hydrocarbons $C_4$'s, or $C_4+$ hydrocarbons. These aliphatic streams are produced in a variety of petroleum refinery operation such as catalytic cracking of gas oil or the like. The dry alkanol feedstream should preferably have a purity of about 99.8 wt%. Suitable alkanols include lower aliphatic $C_1$-$C_4$ primary or secondary alcohols, but preferably methanol.

The reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149-152, discusses the technology. Preferred catalysts are polymeric sulfonic acid exchange resin such as Amberlyst 15 and zeolites such as zeolite Beta and ZSM-5.

In the etherification process it is known that alkanol and iso-olefins may be reacted in equimolar quantities or either reactant may be in molar excess to influence the complete conversion of the other reactant. Because etherification is an incomplete reaction the etherification effluent comprises unreacted alkanol and unreacted hydrocarbons. On a stoichiometric equivalencies basis, equimolar quantities of methanol and iso-olefins are advantageous but an excess between 2 and 200% of either component can be passed to the etherification reaction unit. In the present invention, the molar ratio of alkanol to iso-olefin, such as methanol to iso-butylene, can be between 0.7 and 2, but preferably the molar ratio is 1 for methanol to isobutylene. Advantageously, the excess methanol may be about 40% or more when the hydrocarbon feedstream comprises significant quantity of isoamylenes, but equimolar quantities are preferred when the hydrocarbon feedstream iso-olefin component consists essentially of $C_4$ hydrocarbons.

Iso-olefins or isoalkenes in this invention are those having the formula $R_2C=CH_2$ or $R_2C=CHR$. Alkanols which may be used in the present invention include methanol, ethanol, 1-propanol, isopropanol, 1-butanol and 2-butanol. In this invention oxygenate or lower oxygenates refers to $C_1$–$C_5$ alcohols, ethers, aldehydes, esters and the like.

It is advantageous to convert substantially the entire stream of unreacted alcohol and light olefinic components recovered from etherification effluent by acid zeolite catalysis, thus providing a once-through process without expensive alcohol recycle to the etherification unit. The methanol-containing stream, preferably a vapor stream, may be co-reacted with olefinic light gas and/or other reactive hydrocarbon feedstreams in an oligomerization/aromatization reaction section, as described by Avidan et al. in U.S. Pat. Nos. 4,547,616 and 4,746,762 and by Owen et al. in U.S. Pat. No. 4,827,046 and 4,831,203, incorporated herein by reference. Zeolite conversion technology for upgrading lower aliphatic hydrocarbons and oxygenates to liquid hydrocarbon products, including gasoline boiling range hydrocarbons and aromatics, is well known. Commercial Methanol-to-Gasoline (MTG), methanol-to olefins (MTO), Mobil Olefin to Gasoline/Distillate (MOG/D) and conversion of olefins and paraffins to aromatics (M-2 Forming) processes employ shape selective medium pore zeolite catalysts. It is understood that the present zeolite conversion unit operation can have the characteristics of these catalysts and processes to produce a variety of hydrocarbon products, especially liquid aliphatics and aromatics in the $C_5$–$C_9$ gasoline range. The zeolite catalyzed conversion processes can be run in fixed, fluidized or moving catalyst beds.

The various reactions which take place in the zeolite conversion reactor include oligomerization, alkylation, dehydrocyclization, isomerization, redistribution and cracking. These include exothermic and endothermic reactions, which can be thermally balanced to require little or no heat exchange to maintain process reaction temperature in the fluidized bed. Mixed hydrocarbons from FCC operations, following the etherification and effluent separation, can be selected or modified to include a balance of olefins and paraffins to achieve the desired thermodynamic properties.

Under conditions of high pressure $C_3$ and $C_4$ paraffins are converted to higher hydrocarbons in contact with zeolite catalyst. In U. S. Pat. No. 4,754,100, incorporated herein by reference, it is disclosed that propane when mixed with a controlled amount of mono-olefin is effectively converted with unexpectedly high selectivity to a mixture rich in normal butane, isobutane, pentanes and $C_6+$ aliphatics by contact under a specific set of operating conditions with certain intermediate pore size acid zeolites. In particular, this process provides for the production of $C_4+$ hydrocarbons from a mixture of propane and an amount of lower molecular weight mono-olefin sufficient to increase reaction rate for propane. The preferred process comprises contacting, preferably in the absence of added hydrogen and at a pressure above about 3400 kPa, a feed consisting essentially of propane and a mono-olefin with a catalyst comprising a crystalline alumino-silicate zeolite having a silica-to-alumina ratio of at least 12 and a Constraint Index of 1 to 12, the process reaction being conducted under a combination of conditions of temperature, pressure, and space velocity effective to convert at least 10% of the propane to a mixture of hydrocarbons that contain butanes in an amount equal to at least 35 wt. % of the converted propane.

It has also been found that n-butane is converted directly to propane and gasoline and with no substantial formation of methane by contact with certain intermediate pore size zeolites such as high activity HZSM-5 or zeolite Beta under specified conversion conditions including a pressure of at least 2100 kPa and preferably a relatively low temperature of not more than 800° F. (427° C.). In particular, this process provides a simple catalytic process for the production of propane and gasoline by contacting in the absence of added hydrogen at a temperature of 475° F. (246° C.) to about 800° F. (427° C.) and at a pressure of 600 (4200 kPa) to about 2000 psig (14,000 kPa) a feed consisting essentially of n-butane or iso-butane with a catalyst comprising a crystalline zeolite having a silica-to-alumina ratio of at least 12 and a Constraint Index of 1 to 12, said contacting being conducted under a combination of conditions of temperature, pressure, and WHSV effective to convert about 25 wt % to about 70 wt % of said butane to a mixture of propane and heavier hydrocarbons, with no substantial conversion to hydrocarbon by-products having less than three carbon atoms.

Under similar conditions, in addition to the foregoing conversions of paraffins to higher hydrocarbons at high severity conditions in contact with high activity ZSM-5 catalyst, it has been disclosed (U.S. Pat. No. 4,899,008) that coprocessing of light paraffins with benzene or toluene, or other alkylatable aromatics, in the absence of hydrogen, at pressures of several hundred pounds (above 2100 kPa), but preferably at pressures above about 5000 kpa and temperatures of 600°–900° F. (315°–482° C.), results in the formation of alkyl aromatics, indicative of the incorporation of paraffin moieties into the aromatic nucleus. With H-ZSM-5 catalyst, propane/benzene mixtures give up to 80% conversion with about 75% selectivity to $C_7+$ aromatics.

A preferred catalyst for the aromatic alkylation process using light paraffins is H-ZSM-5-B with a $SiO_2$ to $Al_2O_3$ ratio of 40 and a high alpha value of about 500. The catalyst can be employed in a fixed bed or fluidized bed reactor. "Alpha value", or "alpha number", is a measure of zeolite acidic functionality and is more fully described together with details of its measurement in U.S. Pat. No. 4,016,218, *J. Catalysis*, 6, pp. 278–287 (1966) and J. Catalysis. 61, pp. 390–396 (1980). In the alkylation of aromatics as described herein alpha values in excess of 200 are preferred.

In the following Example 1, the alkylation of aromatics using light paraffins and high alpha value ZSM-5 catalyst is illustrated.

EXAMPLE 1

In a fixed bed reactor containing 1/16 inch extrudate particles of H-ZSM-5-B having an alpha value of about 500, a 50/50 weight percent mixture of propane and benzene is reacted at a weight hourly space velocity (WHSV) of about 3, temperature of about 800° F. (427° C.) and pressure of 800 psig (5600 kPa). At a total weight percent conversion of 73.6, the following product distribution and selectivity is achieved:

| Product Distribution, Wt % | |
|---|---|
| $C_1$ | 5.7 |
| $C_2$ | 9.4 |
| $C_3$ | 16.4 |
| $C_4$ | 2.8 |
| Benzene | 10.0 |
| Toluene | 22 |
| $C_8$ aromatics | 18.3 |
| $C_9+$ aromatics | 14.7 |
| Selectivity | |
| $C_1 + C_2$ | 20.6 |
| $C_4-C_6$ | 4.3 |
| $C_7+$ aromatics | 75.1 |

In the present invention the foregoing processes are combined in a synergistic and novel manner to produce high octane gasoline rich in alkylated aromatics and a high octane gasoline rich in tertiary alkyl ethers. The unique process configuration permits the utilization of inexpensive $C_3+$ feedstock containing paraffins as a feedstream to the etherification step and also utilizes benzene rich gasoline streams as a source of aromatics for the alkylation step. Aromatic gasoline from naphtha reforming is a particularly useful source of aromatics for the alkylation step of the instant invention. Thus, the integrated process avoids the costs associated with separating and recycling unreacted alkanol to the etherification reactor; utilizes a lower cost $C_3+$ etherification feedstock containing propane; and upgrades an environmentally troublesome refinery product, benzene, to an acceptable gasoline component by alkylation of benzene, and other light aromatics, using paraffins from the etherification feedstream as alkylating agent and using high alpha value H-ZSM-5 as catalyst.

Referring to FIG. 1, a preferred embodiment of the present invention is illustrated. A continuous stream of $C_3+$ olefinic and paraffinic hydrocarbon is introduced via conduit 10 to a first reactor 20 and mixed with dry methanol (MeOH) feedstock introduced via conduit 12. The combined streams are pressurized to about 1190 kPa (170 psig), heated to a temperature of about 55° C. (130° F.) for conversion of methanol in contact with acid etherification catalyst, preferably solid polysulfonic acid resin such as sulfonated vinyl aromatic resins.

The reactor effluent stream containing MTBE, methanol and unreacted light hydrocarbons is preheated and fed 35 to debutanizer fractionation tower 40. In separation unit 40 the $C_5+$ methyl tert-alkyl ether product is recovered 41 as a liquid product, along with byproduct dimer or other heavier hydrocarbons in the effluent. Tower overhead liquid 43 comprising unreacted $C_4-$ light hydrocarbons and methanol is pumped and preheated before being passed to alkylation and upgrading reactor 50 as a liquid via conduit 42. An aromatic $C_6-C_7$ feedstream is passed to reactor 50 via conduit 44 from an upper-portion of splitter 55. In the zeolite catalytic alkylation and conversion unit 50 under high pressure above about 3400 kPa and a temperature of about 800° F. (427° C.), aromatics, $C_4-$ paraffins, olefins and methanol are converted to higher hydrocarbons and alkyl aromatics. Effluent may be fractionated in a debutanizer (not shown) to recover a gasoline product stream 47, and $C_4-$ hydrocarbons 48. The gasoline product stream 47 is passed to a bottom portion of the splitter 55 which also receives in a mid-portion an aromatic rich gasoline stream 49, such as a reformate, containing light aromatics, particularly benzene. Streams 47 and 49 are fractionated in splitter 55 to provide the benzene-rich feedstream 44, a heavy aromatic rich gasoline stream 51, and a $C_5+$ light gasoline stream 52. Preferably, unreacted $C_3-C_4$'s from stream 48 can be recycled to reaction zone 50.

In another embodiment of the present invention the principal processes of etherification and high pressure conversion of unreacted hydrocarbons may be combined with a low severity zeolite catalyzed conversion to provide a process that converts a major portion of alkenes in the hydrocarbon feedstream to gasoline components. This combination is illustrated in FIG. 2.

Figure 2:
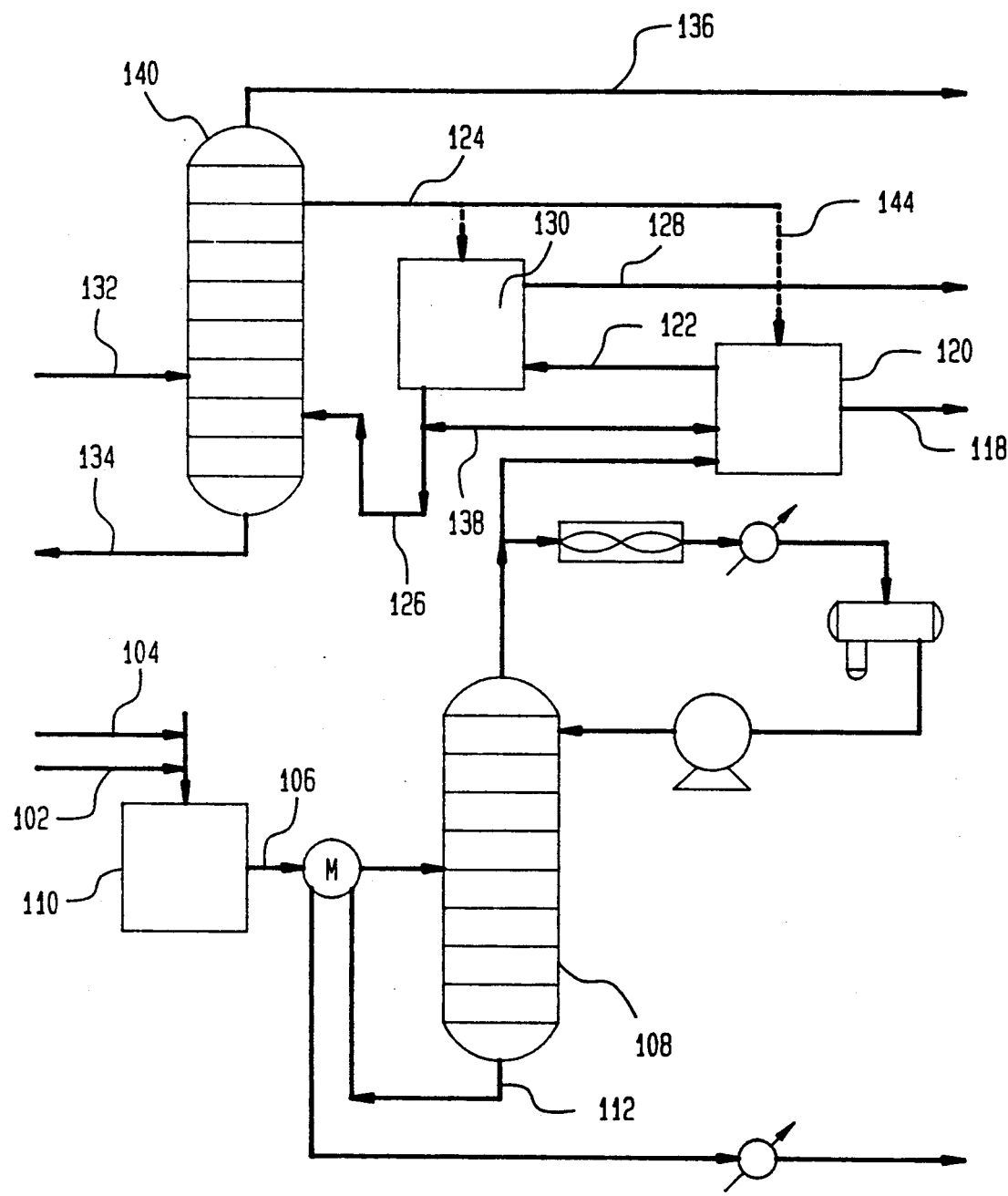
FIG. 2 is a schematic diagram of the present invention integrating etherification, low to moderate pressure conversion of alkanol and hydrocarbon and high pressure conversion of hydrocarbons to alkylated aromatics.

Referring now to FIG. 2, the major conversion processes are carried out in etherification reactor 110, low to moderate pressure alkanol and olefin conversion reactor 120 and high pressure $C_3-C_4$ paraffin conversion and aromatics alkylation reactor 130. A $C_3+$ iso-olefin rich hydrocarbon stream 102 is combined with alkanol feedstream 104, e.g., methanol or isopropanol, and passed to the etherification reactor where etherification of iso-olefins is carried out in contact with acidic catalyst. The effluent from the etherification reaction is passed via conduit 106 to debutanizer 108. From the debutanizer a liquid stream 112 is separated comprising $C_5+$ gasoline rich in alkyl tertiary alkyl ether, such as MTBE. The overhead vapor stream 114 from the debutanizer is passed to the zeolite conversion zone 120 wherein unreacted alkanol and olefins in the vapor stream are converted to higher hydrocarbons at a temperature of about 325° C. and 925 kPa. From the conversion zone 120 a $C_5+$ gasoline stream 118 is separated and recovered. The $C_3-C_4$ stream 122 from the low severity conversion zone containing paraffins and olefins is passed to the high severity high pressure zone 130 in conjunction with a portion of stream 124 from splitter 140 containing paraffins and $C_6-C_7$ aromatics, but preferably comprising between 15% and 50% benzene. Another portion of stream 124 is passed 144 to the olefin conversion reactor 120. The conversion of olefins in zone 120 is not complete and leaves some $C_3-C_4$ olefins in the effluent to enhance propane conversion in the high pressure reactor. In the zeolite catalytic alkylation and conversion unit 130 under high pressure above about 3400 kPa and a temperature of about 800° F. (427° C.), aromatics, $C_4-$ paraffins and olefins are converted to higher hydrocarbons and alkyl aromatics. Effluent may be fractionated in a debutanizer (not shown) to recover a gasoline product stream 126, and $C_4-$ hydrocarbons 128. The gasoline product stream 126 is passed to a bottom portion of the splitter 140 which also receives, in a mid-portion thereof, an aromatic rich gasoline stream 132, such as a reformate, containing alkylatable aromatics, particularly benzene. The combined streams 126 and 132 are separated in splitter 140 to provide the aromatic feedstream 124, a $C_8+$ heavy aromatic rich gasoline stream 134, and a $C_5+$ light gasoline stream 136. Preferably, unreacted $C_3-C_4$'s can be recycled to reaction zone 130.

The olefin conversion reactor 120 can, optionally, contain HZSM-23 catalyst. Under these conditions the $C_4$ stream 128 from the alkylation reactor 130 can be upgraded by passing all or a portion of the stream to reactor 120.

Optionally, the $C_5+$ effluent from the low severity reactor zone 118 may also be passed via conduit 138 to combine with the $C_5+$ fraction from zone 130 and fractionated in system 140.

While the overall integrated process herein disclosed provides a novel combination of process steps that refurbishes the utility of benzene containing gasoline streams and light paraffinic hydrocarbon refinery streams, the utility of the process is particularly augmented by the discovery of the reformate splitter design. This design combines in a single vessel the means to separate the aromatic reformate to provide the feedstream to the alkylation unit with the means to separate the alkylation effluent $C_5+$ product and produce useful heavy and light gasoline products. As a consequence, the overall process costs are advantageously effected. Also, the aromatic alkylation unit, as shown in FIG. 3, comprises a novel design that augments the usefulness of the discovery herein disclosed.

Figure 3:
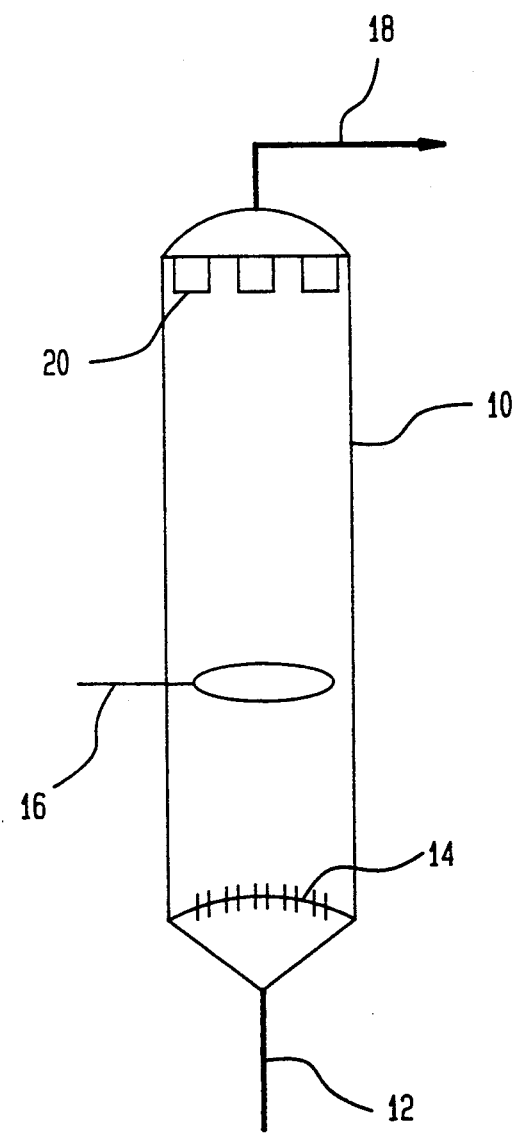
FIG. 3 is a schematic drawing of the novel aromatic alkylation reactor of the present invention.

Referring to FIG. 3, the aromatic alkylation reactor comprises a vertical vessel 10 for containing zeolite catalyst particles. The vessel preferably has a height to diameter ratio between 1 and 10. Reformate is fed 12 to a bottom inlet means below a grid plate 14 and light paraffins and olefins, or paraffins, olefins and alkanol, are fed to the reactor through conduit 16. The vessel operates under a superficial velocity between 2-6 feet per second and product is removed overhead through conduit 18. Filters 20 are provided to contain catalyst particles.

While the instant invention has been described by specific examples and embodiments, there is no intent to limit the inventive concept except as set forth in the following claims.

What is claimed is:

1. A continuous integrated process for producing hydrocarbon streams comprising $C_5+$ gasoline rich in alkyl tertiary alkyl ether and $C_5+$ alkylated aromatic rich gasoline, comprising the steps of:
   (a) contacting alkanol and $C_3+$ aliphatic hydrocarbon stream containing alkanes and alkenes rich in iso-olefins with acid etherification catalyst under iso-olefin etherification conditions in an etherification reaction zone;
   (b) separating etherification effluent from step (a) to recover an overhead stream comprising unreacted alkanol plus $C_4-$ aliphatic hydrocarbons and a liquid product stream comprising $C_5+$ gasoline containing alkyl tertiary-alkyl ether;
   (c) contacting said overhead stream and a feedstream containing light aromatic hydrocarbons in an alkylation reactor containing acidic, medium pore metallosilicate catalyst under alkylation conditions and conversion conditions sufficient to convert alkanol, alkane and alkene to higher hydrocarbons said conditions comprising a temperature of about 200° C. to 400° C. and a pressure above about 3400 kPa; and
   (d) separating step (c) reaction products and recovering said $C_5+$ alkylated aromatic rich gasoline and a stream comprising $C_4-$ hydrocarbons.

2. The process of claim 1 wherein said alkanol feedstock includes methanol, ethanol, 1-propanol, isopropanol, 1-butanol, 2-butanol and mixtures thereof.

3. The process of claim 1 wherein step (c) conversion conditions comprise a temperature of about 200° C. to 370° C., a pressure above about 3400 kPa, a weight hourly space velocity of about 0.1 to 30, and in the essential absence of hydrogen.

4. The process of claim 1 wherein step (c) catalyst has the structure of ZSM-5 or zeolite Beta.

5. The process of claim 1 wherein the alkanol feedstock comprises dry methanol.

6. The process of claim 1 wherein step (b) alkyl tertiary-butyl ether comprises methyl tertiary butyl ether.

7. The process of claim 1 wherein said etherification catalyst comprises acidic zeolite or sulfonated vinyl aromatic resins.

8. A continuous process for converting lower aliphatic alkanol feedstock and aliphatic hydrocarbon feedstream containing $C_3+$ alkane and alkene rich in iso-olefins to alkyl tertiary-alkyl ether rich $C_5+$ gasoline boiling range hydrocarbons and $C_5+$ alkylated aromatic rich gasoline, comprising the steps of:
   (a) contacting alkanol and said aliphatic hydrocarbon stream rich in iso-olefins under iso-olefin etherification conditions in an etherification reaction zone containing acid etherification catalyst;
   (b) separating etherification effluent from step (a) to recover an overhead stream comprising unreacted alkanol plus $C_3$-$C_4$ aliphatic hydrocarbons and recovering a liquid product stream containing $C_5+$ alkyl tertiary-alkyl ether rich gasoline;
   (c) contacting said overhead stream with acidic, medium pore metallosilicate catalyst under low severity alkanol and hydrocarbon conversion conditions;
   (d) separating step (c) effluent and recovering a stream comprising $C_5+$ gasoline boiling range hydrocarbons and a stream containing unreacted $C_3$-$C_4$ hydrocarbons;
   (e) contacting step (d) $C_3$-$C_4$ hydrocarbon stream and a feedstream containing $C_7-$ aromatic hydrocarbons in an alkylation reactor containing acidic, medium pore metallosilicate catalyst under conversion conditions sufficient to convert alkane and alkene to higher hydrocarbons and alkylate said aromatic hydrocarbons, said conditions comprising a temperature of about 200° C. to 400° C. and a pressure above about 3400 kPa, and recovering $C_5+$ gasoline boiling range hydrocarbons; and
   (f) separating step (e) reaction products and recovering said $C_5+$ alkylated aromatic rich gasoline and a stream comprising $C_4-$ hydrocarbons.

9. The process of claim 8 wherein said alkanol feedstock includes methanol, ethanol, 1-propanol, isopropanol, 1-butanol, 2-butanol and mixtures thereof.

10. The process of claim 8 wherein step (e) conversion conditions comprise a temperature of about 200° C. to 427° C., a pressure above about 3400 kPa, a weight hourly space velocity of about 0.1 to 30, and in the essential absence of hydrogen.

11. The process of claim 8 wherein step (c) and (e) catalyst has the structure of ZSM-5.

12. The process of claim 8 wherein the alkanol feedstock comprises dry methanol.

13. The process of claim 8 wherein step (b) alkyl tertiary-alkyl ether comprises methyl tertiary butyl ether.

14. The process of claim 8 wherein step (b) aliphatic hydrocarbons comprise $C_3$-$C_4$ hydrocarbons and said liquid stream contains alkyl tertiary butyl ether and alkyl tertiary amyl ether.

15. The process of claim 14 wherein said alkanol comprises methanol.

16. The process of claim 8 wherein said etherification catalyst comprises acidic zeolite or sulfonated vinyl aromatic resins.

17. The process of claim 1 or 8 comprising the further steps of passing said $C_5+$ alkylated aromatic rich gasoline to a fractionator in conjunction with a gasoline feedstream rich in light aromatic hydrocarbons; separating an overhead stream comprising $C_5$-$C_6$ gasoline, a bottom stream comprising alkylated aromatic rich gasoline and a stream comprising $C_6$-$C_7$ alkylatable aromatics; and passing said alkylatable aromatic stream to said alkylation reactor whereby said $C_5+$ alkylated aromatic rich gasoline is produced.

18. A continuous integrated process for producing hydrocarbon streams comprising $C_5+$ gasoline rich in alkyl tertiary alkyl ether and $C_5+$ alkylated aromatic rich gasoline, comprising the steps of:

(a) contacting alkanol and $C_3+$ aliphatic hydrocarbon stream containing alkanes and alkenes rich in iso-olefins with acid etherification catalyst under iso-olefin etherification conditions in an etherification reaction zone, (b) separating etherification effluent from step (a) to recover an overhead stream comprising unreacted alkanol plus $C_4-$ aliphatic hydrocarbons and a liquid product stream comprising $C_5+$ gasoline containing alkyl tertiary-alkyl ether;

(c) contacting said overhead stream and a feedstream containing light aromatic hydrocarbons rich in benzene in an alkylation reactor containing acidic, medium pore metallosilicate catalyst under alkylation conditions and conversion conditions sufficient to convert alkanol, alkane and alkene to higher hydrocarbons with no substantial formation of methane, said conditions comprising a temperature of about 200° C. to 400° C. and a pressure above about 3400 kPa; and (d) separating step (c) reaction products and recovering said $C_5+$ alkylated aromatic rich gasoline and a stream comprising $C_4-$ hydrocarbons.

(e) passing said $C_5+$ alkylated aromatic rich gasoline to a fractionator in conjunction with a gasoline feedstream containing light aromatic hydrocarbons rich in benzene;

(f) separating an overhead stream comprising $C_5$-$C_6$ gasoline, a bottom stream comprising alkylated aromatic rich gasoline and a stream comprising $C_6$-$C_7$ alkylatable aromatics rich in benzene;

(g) passing said $C_6$-$C_7$ alkylatable aromatic stream to said alkylation reactor whereby said $C_5+$ alkylated aromatic rich gasoline is produced.

* * * * *